United States Patent [19]

Cosman

[11] 4,206,761
[45] Jun. 10, 1980

[54] PRESSURE-BALANCED TELEMETRIC PRESSURE SENSING METHOD

[76] Inventor: Eric R. Cosman, 872 Concord Ave., Belmont, Mass. 02178

[21] Appl. No.: 895,955

[22] Filed: Apr. 13, 1978

Related U.S. Application Data

[62] Division of Ser. No. 697,951, Jun. 21, 1976, abandoned.

[51] Int. Cl.² .................................. A61B 5/00
[52] U.S. Cl. .................... 128/660; 128/748; 128/675; 73/701; 73/717; 73/718; 73/722
[58] Field of Search ............. 128/673, 675, 748, 660; 73/701, 708, 716–719, 722

[56] References Cited

U.S. PATENT DOCUMENTS

| 3,034,356 | 5/1962 | Bieganski et al. | 128/748 |
| 3,038,465 | 6/1962 | Allard et al. | 128/675 |
| 3,720,108 | 3/1973 | Freitag | 73/722 |
| 3,722,373 | 3/1973 | Beach et al. | 73/716 X |
| 3,724,275 | 4/1973 | Battaglini et al. | 73/716 |
| 3,727,463 | 4/1973 | Intraub | 73/398 R |
| 3,757,770 | 9/1973 | Brayshaw et al. | 128/748 X |
| 3,853,117 | 12/1974 | Murr | 128/748 X |
| 3,859,484 | 1/1975 | Nelson | 73/716 X |
| 3,943,915 | 3/1976 | Severson | 73/406 X |
| 4,014,319 | 3/1977 | Faure | 128/748 |
| 4,026,276 | 5/1977 | Chubbuck | 128/653 |
| 4,067,241 | 1/1978 | Corbett | 73/717 |
| 4,141,348 | 2/1979 | Hittman | 128/748 |

OTHER PUBLICATIONS

Collins, C.C., *IEEE Trans-On Bio.-Med. Engng.* vol. 14, No. 2, Apr. 1967, pp. 74–83.
Atkinson, J. R. et al., *Journ. of Neurosurgery*, 1967, vol. 27, No. 5, pp. 428–432.

Primary Examiner—Kyle L. Howell
Attorney, Agent, or Firm—Richard J. Birch

[57] ABSTRACT

A differential pressure sensing device is fully implanted in the body of a patient to monitor internal pressure such as intracranial pressure. A movable element in the sensor communicates on one side with the internal pressure to be measured and on the other side with an external pressure which is applied by an external pressurizer-control system and which is communicated to the sensor through the intact skin. An imbalance of the two opposing pressures causes a displacement of the movable element which changes a physical characteristic of the sensor, such as the resonant frequency of a tuned L-C circuit. This change is detected outside the body by an external detection system, such as a frequency swept radio frequency oscillator. The external pressure is varied until the external detector senses that the pressures are balanced on the movable element, at which point the external pressure equals the internal pressure, and the former is measured and read out.

42 Claims, 11 Drawing Figures

PRESSURE-BALANCED TELEMETRIC PRESSURE SENSING METHOD

CROSS REFERENCE TO RELATED APPLICATION

This application is a divisional application of Ser. No. 697,951, filed June 21, 1976, now abandoned, by Eric R. Cosman for A Pressure-Balanced Telemetric Pressure Sensing System and Method Therefore.

BACKGROUND OF THE INVENTION

The invention relates to the precision measurement and monitoring of pressures in a confined region and particularly in a living body, such as intracranial pressure in the head, by means of a long-term totally implanted pressure sensor which undergoes a conformational change with pressure and which is coupled through the skin by electromagnetic, acoustic, or mechanical transmission to an external device which detects that change and interprets the pressure. The invention refers additionally to a device which is automatically barometric compensated, has immediate zero point reference check, can be made passive, and is insensitive to barometric or temperature changes.

At the present time there is no such wireless device available for general clinical or research purposes. The uses for such a device in neurosurgery would be immediate in the management of intracranial hypertension, monitoring of intracranial pressure in all cases of intracranial neurosurgery and head trauma, longterm diagnostics for evidence of tumor recurrence, and management of hydrocephalus.

All devices previously proposed have significant shortcomings which make them impractical for widespread, safe, accurate, reliable, and longterm use as intracranial pressure monitors. Most designs involve a tube or wire connection through the skin to an external device, and since this greatly increases the chance of infection and electrical shock to the patient and reduces the patient's mobility, they are hazardous and impractical. Of the devices which are wireless and fully implanted, they usually involve a sealed inner volume containing a fixed amount of gas, this being housed in a flexible container which deflects under pressure. The major problems with this design aspect are the following: liquids and gases will inevitably diffuse through the membranes and walls of the container causing steady drift of the zero-point reading, and causing an unpredictable error in the device's calibration; changes in barometric pressure will cause significant variations in the body pressure relative to the fixed volume pressure and thus the device's pressure readout must be corrected for barometric pressure changes in the external detection system; a trapped volume of significant size could make it dangerous for a patient to experience atmospheric pressure change, such as those found in air travel, for fear of rupturing the device; and temperature changes in the patient will cause changes in the trapped volume and resultant errors in the pressure reading. Previous totally implanted designs provide no means to check their zero-pressure calibration after implantation and thus no means to determine diffusion or temperature drifts in the readings nor any check of the proper function of the device, which is essential for long and shortterm implantation. Most previous designs are of complex construction involve high tolerance parts and assembly, and are not amenable to calibration standardization; all of which make them expensive, inaccurate, and unsuitable for simple and general application.

Accordingly, some of the principal objects of the present invention are the following:
(1) To provide a pressure detector which can be implanted for an indefinite period under a fully intact skin with no wire or tube connections to the exterior so as to reduce infection and electrical shock hazard, and to read pressures in inaccessible spaces in the body, such as intracranial pressure, with an accuracy of 5 to 10% or better.
(2) To eliminate or make insignificant all inaccuracies, and dependencies on a trapped volume of gas or fluid in the device, to make the pressure readings insensitive to drifts from membrane permeability, barometric change and temperature variation, and to eliminate the hazard of rupturing the device during air travel.
(3) To provide automatic barometric compensation as a built-in feature of the implanted device.
(4) To provide a means of easily and instantly checking the zero-pressure calibration of the device.
(5) To provide a sufficiently fast dynamic response to enable observation of variations in the body pressure due to heart rate, respiration, and any other physiological changes.
(6) To allow a simple calibration standardization of the implant.
(7) To allow the implanted device to be of simple, passive, compact, and low cost construction so as to be implanted permanently and to function properly for indefinitely long periods.
(8) To make the system amenable to telemetry over long distances so as to monitor pressures in a freely moving patient.

SUMMARY OF THE INVENTION

The invention enables the precision measurement of pressure inside the living body without a break through the skin or wires or tubes through the skin and involves a novel differential pressure sensing device fully implanted in the body, an external detection system which can interrogate the implanted sensor in the body, an external pressurizing system which can control and measure pressure which is applied to the skin in the region of the implanted sensor, and a means of displaying and recording the pressure applied by the external pressurizing-control system. The principle of operation of the invention is the following: the fully implanted sensor, which is covered by a completely intact skin, contains a movable element which feels the internal bodily pressure to be measured on one side and an external pressure applied through the intact skin over the sensor by the pressurizing-control system on the other side, so that its equilibrium position corresponds to a balancing or equality of the two pressures. This equilibrium condition or balanced position of the movable element is detected with an external detection system by means of electromagnetic, acoustic, radiation, mechanical, or other methods of coupling across the skin to the implanted sensor. The externally applied pressure on the skin, which corresponds to the internal body pressure when the balance condition is attained, can be measured with high precision and may be controlled manually or automatically and varied until the balanced condition is detected. The implanted sensor can have a built-in fiducial point corresponding to the pressure balanced position of the movable element which can be checked at any time by pressing manually on the skin covering the sensor, thereby bringing the movable element to the fiducial position and allowing the external detection system to be adjusted or "zeroed" relative to it. In operation, a deviation from this reference position caused by a difference in pressures across the implanted sensor is detected by external detection system and an associated error signal can be used to increase or decrease the externally applied pressure so as to equalize the internal and external pressures. In this way the external pressurizing-control system can be made to track variations in the internal pressure to be measured.

A specific illustration of this invention will be given in which the implanted sensor contains a passive L-C tank circuit, the inductance, capacitance, or both of which are pressure dependent. The resonant frequency of this circuit is thus pressure dependent and is detected by the external detection system in order to determine if the system is or is not in the pressure balanced condition, which information may be used to provide an error signal to the external pressurizing-control system. The external detection system in this case is coupled electromagnetically to the implanted sensor and may embody a swept frequency, energy dip oscillator to detect the sensor's resonant frequency. Several other ways of implementing this invention concept will be cited. Several illustrative embodiments of the invention will be shown which have application in measuring and monitoring intracranial pressure.

The present invention has all of the novel and unique advantages of the wireless and tubeless pressure measuring device described in U.S. patent application Ser. No. 697,948, filed on June 21, 1976, by the present inventor and in addition has several other novel features and differences. Like the said other invention, the present invention makes use of pressure transmission through the fully intact skin and does not compress a trapped volume of gas in the sensor, and this eliminates problems of zero-point calibration drift, barometric compensation, and rupture hazard. However, the said other invention uses only atmospheric external pressure and relies further on a spring in the sensor to provide a calibrated displacement of a movable element in the sensor for a given internal pressure to be measured. In contrast, the present invention eliminates the spring force by applying an externally controlled pressure to the sensor across the skin and thus makes the pressure measurement at only one position corresponding to zero displacement of the movable element in the sensor; thus placing the burden of pressure calibration in the external equipment and eliminating inaccuracies due to surface tension effects at non-zero displacements. The method of the present invention has the resulting advantages of greater accuracy, range of pressure measurement, linearity, and simplicity of sensor construction.

DESCRIPTION OF THE DRAWINGS

Further objects, advantages, and aspects of the present invention can be gained from the following detailed description, illustrative drawings, and various embodiments and implementations. Illustrations will be given for measuring intracranial pressure although uses in other parts of the body are possible. In the following drawings similar reference characters represent similar parts.

Figure 1:
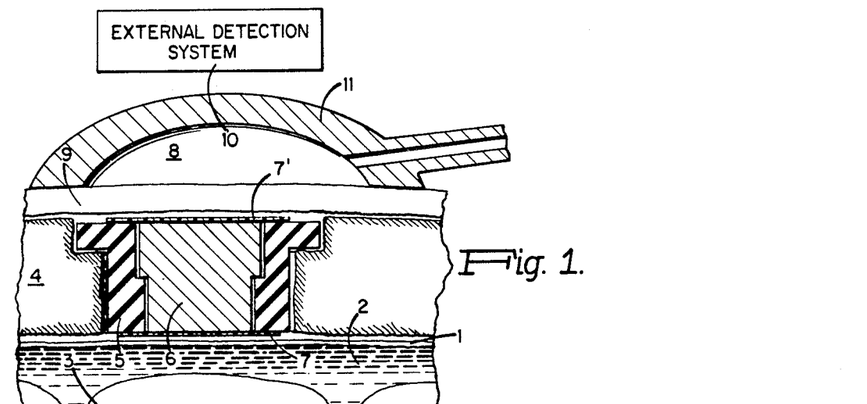
FIG. 1 shows a schematic, vertical sectional view of an implanted pressure sensor and related external systems being used to measure intracranial pressure in a living human being.

FIG. 1 illustrates the major elements of the implanted pressure sensor, used in this example as a monitor of epidural intracranial pressure if the dural membrane 1 is intact or of cerebrospinal fluid 2 pressure that surrounds the brain 3 if the dura 1 is cut. The sensor, which is inserted into a burrhole drilled in the skull 4 comprises a housing 5 which has a through opening in it in which moves a movable element 6. An inner flexible diaphragm 7 attached to the housing 5 communicates the intracranial pressure $P_{ICP}$ inside the skull to one side of the movable element 6 and an outer flexible diaphragm 7' communicates the external pressure $P_{EXT}$ in the region 8, which is transmitted across the intact scalp 9, to the other side of movable element 6. By this system a difference $\Delta P = P_{ICP} - P_{EXT}$ will cause a force imbalance on element 6, and for example if $\Delta P$ is positive that net force will cause the movable element and flexible diaphragms 7 and 7' to be displace upward. If $P_{EXT}$ is then increased so as to balance the pressure $P_{ICP}$, i.e. $P_{EXT} = P_{ICP}$ then $\Delta P = 0$ and the movable element 6 is restored to its balanced position. The balanced position of movable element 6 relative to the body 5 is indicated by a shoulder stop in FIG. 1, but other physical or electromagnetic fiducials are possible. A displacement of 6 relative to 5 can be made to cause changes in some physical, electrical, or magnetic characteristic of the sensor. Those changes can be detected by an external detection system 10 which is coupled to the implanted sensor by electromagnetic, acoustic, or other means across the skin, but not through the skin as by a tube or wire. The balance position may be predetermined and calibrated during construction so that it can be easily recognized after implantation by some known value of an eleectrical or mechanical characteristic of the sensor. Alternatively, with a mechanical stop to interrupt the downward movement of 6 relative to 5 as in FIG. 1, pressing on the skin just above diaphragm 7' will bring the sensor into its balanced condition and provides an instant zero-point calibration and check of the sensor and detector systems $\Delta P = 0$ reference long after implanatation. In operation external detector 10 interrogates the implanted sensor and determines if a balanced condition, $\Delta P = 0$, or imbalanced condition, $\Delta P \neq 0$, exists in the sensor. With elevating intracranial pressure $\Delta P$ will become more positive temporarily. This will be detected by 10 and $P_{EXT}$ will be increased by an external pressurizer attached to the pressure applicator 11 until detector 10 detects a balanced condition $\Delta P=0$ at which point $P_{EXT}=P_{ICP}$ and may be recorded or read out. No particular calibration of $\Delta P$ versus displacement of element 6 relative to the frame is necessary although this may be built-in by spring loading 6, for added flexibility of measurement. The pressure balance method described here reduces the degree of complexity of the transsensor construction to only that necessary to detect deviations from a balance position rather than a calibrated pressure versus displacement characteristic. Thus, the burden of accurate pressure detection instrumentation lies external to the body where it is easily implemented. Two membranes 7 and 7' are shown in FIG. 1, however, as shown below, one membrane may be sufficient as long as it allows proper communication of $P_{ICP}$ and $P_{EXT}$ to movable element 6. Common implementations of the coupling of the motion of 6 to the external detector 10 are by use of a passive L-C circuit; this will be discussed below.

Figure 2:
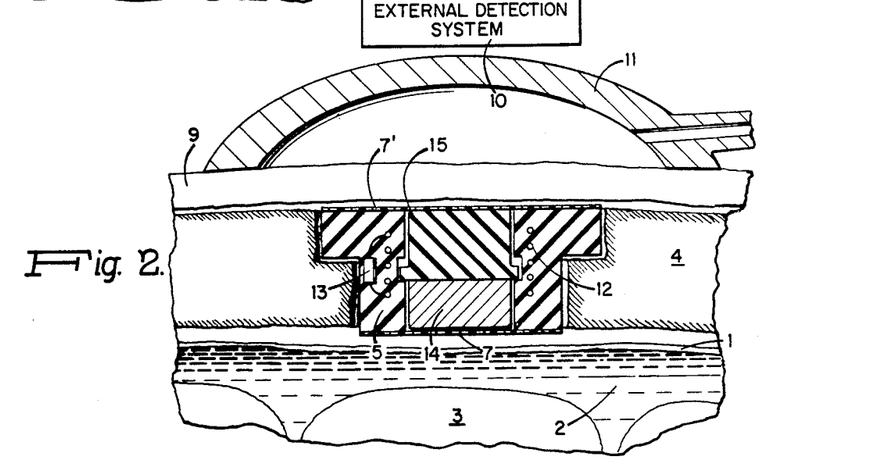
FIG. 2 shows a view in vertical section of a more specific design of the invention concept of FIG. 1 involving a passive L-C resonant circuit in the sensor.

Referring to FIG. 2, a specific embodiment of the basic invention concepts of FIG. 1 is shown. The cylindrical body 5 comprises an insulating plastic such as nylon or "Lexan" and has an upper flange so that it seats in a standard burr hole in the skull 4. A fixed coil 12 and capacitor 13 are embedded in the body 5 to form a parallel L-C tank circuit. A magnetic slug 14 moves in a cylindrical hole through the body 5 and is attached to a coaxial cylinder 15, made of a non-magnetic material to the movable element 6 of FIG. 1. The two diaphragms 7 and 7' are made of thin flexible plastic material, may be convoluted for added flexibility, sealed to the body 5, and contact the ends of cylinders 14 and 15. The diaphragms 7 and 7' plus cylinders 14 and 15 form a dual motion-coupled membrane system with end-for-end symmetry such that P ICP is felt on one end, $P_{ATM}$ is communicated through the intact skin is felt on the other end, and the external force on the cylinders 14 and 15 is directly proportional to the difference $\Delta P=P_{ICP}-P_{ATM}$. When $P_{ICP}$ is greater than $P_{ATM}$ the magnetic slug 14 will move upward relative to coil 12 thus changing the inductance of the coilmagnetic slug system. This in turn will cause a change in the resonant frequency of the L-C tank circuit, which is detected outside the body by an external detector system 10 described below. The coaxial cylinder 15 of non-magnetic material is attached to the ferrite and is shown here to have a stop-flange which comes against a shoulder in the frame 12 when the pressure balance $\Delta P=0$ is attained, as shown, and this will correspond to a balanced condition frequency $f_o$ of the resonant circuit. In operation the external pressurizer-control system will increase $P_{EXT}$ in the region 8 just above the sensor until the external detector determines that the frequency $f_o$ is reached; and thus $P_{EXT}$ equals $P_{ICP}$.

Figure 3:
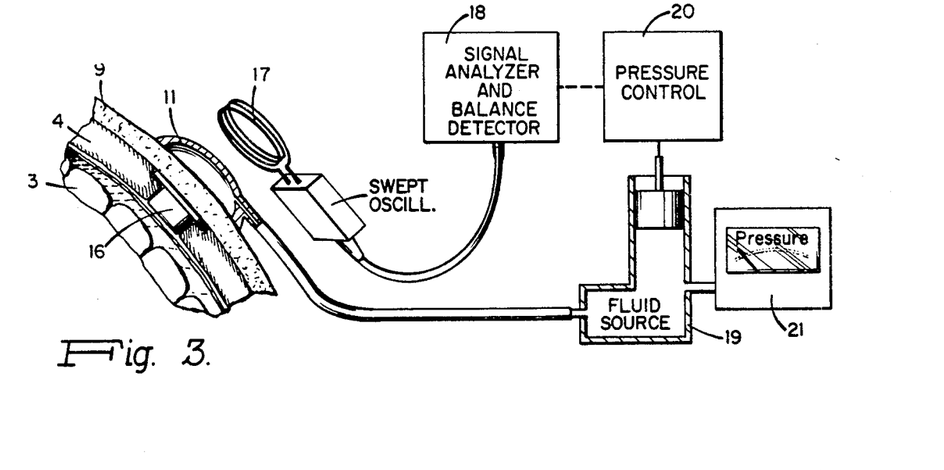
FIG. 3 illustrates implementation of the external detection and external pressurizer-control systems relative to the implanted sensor.

Referring to FIG. 3 means of detecting, tracking, and reading out the intracranial pressure $P_{ICP}$ are illustrated. The resonant L-C circuit in the implanted sensor 16 is coupled electromagnetically to the external detection system which comprised an antenna-oscillator 17 and a signal analyzing circuit and balance pressure detector 18. The oscillator in 17, operating typically at 10 to 100 Mega Hertz, is frequency swept at an audio rate. It experiences a power dip at the sensor's resonant frequency and the analyzer circuit 18 detects this dip and generates an output signal proportional to the associated resonant frequency. Such "grid-dip" oscillator detectors are well known and need not be described in detail here. The pressurizer-control system consists of a source of fluid 19 under pressure $P_{EXT}$ which is connected by a tube to pressure cuff 11, a pressure control means 20 for varying $P_{EXT}$ in 19 and 11, and a means 21 of measuring and reading out the pressure in 19. The pressure control means 20 would increase the pressure in 19, and thus $P_{EXT}$ applied to sensor 16 through the skin, until signal analyzer 18 detects that the frequency corresponding to a pressure balance on the sensor has been reached. At this point $P_{ICP}=P_{EXT}$ and is readout of 21. Pressure controller 20 may be manually operated or coupled to the output of 18 for automatic tracking of $P_{ICP}$. The pressure cuff 11 can be a flexible bag integrally attached to 17.

There are several other notable novel features and ancillary points to be made about the design of FIG. 2. End-for-end symmetry of the dual motion-coupled diaphragm system, convoluted flexible diaphragms, and the very small innerspace $V_{IN}$ which is required only for wall clearance of the cylinders 14 and 15 eliminate drift due to diaphragm permeability, aberrations due to barometric pressure change, and hazard of rupture during air travel. If the innerspace volume $V_{IN}$ is initially filled with air and if diffusion of this gas outward and of fluid inward after implantation cause a reduced pressure $P_{IN}$ in $V_{IN}$, then because of end-for-end symmetry of 7, 7', 14 and 15 the forces on diaphragms 7 and 7' will be the same function of $P_{ICP}-P_{IN}$ and $P_{ATM}-P_{IN}$, and thus the net force, and associated displacement, of cylinder 14 and 15 will depend only on $\Delta P=P_{ICP}-P_{ATM}$ and not on $P_{IN}$. Should a sudden change $\partial P_{ATM}$ in barometric pressure, $P_{ATM}$, occur as in air flight the change in $V_{IN}$ will be $\partial V_{IN} \cong = \partial P_{ATM}/P_{ATM} V_{IN}$ and if $V_{IN}$ is very small, so will be $\partial V_{IN}$. Thus the perturbation on and danger of rupturing of diaphragms 7 and 7' will be accordingly small, and again end-for-end symmetry will cancel any effect on the detection of $\Delta P$. The same argument applies to changes in $P_{IN}$ or $V_{IN}$ because of changes in surrounding temperature. The novel features of the application of an external balancing pressure to the sensor through the skin and the provision of a shoulder stop of 14 and 15 against the body 5 at equilibrium position, not only allow an instant zero pressure reference check, but also insures an instant check of the operation of the entire system and correction to any temperature dependent variations in the electro-mechanical characteristics of the sensor. The coil 12 and capacitor 13 can easily be selected for negligible temperature drift and high resonant Q. The cylinders 14 and 15 can be teflon coated and axially suspended on diaphragms 7 and 7' so that friction is minimized and the static and dynamic response and sensitivity are maximized. The design has been demonstrated in implantations to detect differences in intracranial pressure of less than 5 mm of $H_2O$ and to record easily the rapid pressure variations due to heart beat and respiration, these being important clinical indications of a working system which previous designs cannot achieve. The diaphragms 7 and 7' may be arranged co-planar with the dura 1 and scalp 9, respectively, during equilibrium so that surface tension effects of the latter are eliminated and fibrosis of the dura will not occur in long implantations, a problem which has plagued previous designs. A range of clinically observed pressures can be measured with complete linearity. The sensor is cosmetically inobtrusive, lying flat with the scull 4. The design of FIG. 2 can be made less than ½ inch in diameter and as shallow as 3 to 11 mm total height, making them adaptable to infants or small animals as well as adults. The design is intrinsically simple for high volume, low manufacture. It can be made of biocompatible material and covered with a thin silicone rubber enclosure.

It is understood that many variations of the basic concepts disclosed in FIGS. 1, 2 and 3 are possible and included in this disclosure. The sensor may have only one diaphragm, which feels $P_{ICP}$ on one side and $P_{ATM}$ on the other. The movable element, equivalent to 6 in FIG. 1, may be attached to the single diaphragm and the displacement of it and the diaphragm is detected externally. In the dual motion-coupled diaphragm design, the diaphragms 7 and 7' may not be stacked as in FIG. 1, but located at more remote separation. The coupling element 6 may be a rigid mechanical means such as a cylinder or linkage, or may be a fluid transmitted through the body by a tube or channel. The physical characteristic of the sensor which is changed and detected with change of differential pressure $\Delta P = P_{ICP} - P_{EXT}$ may be diverse, and accordingly, so may be the detection means. For example, referring to FIG. 1, the body 5 and movable element 6 may be scatterers or absorbers of mechanical, acoustic, or ultrasonic waves or of electromagnetic waves such as micro waves or infrared radiation and the external detector system 10 may involve a source, interferometer, echo detector, frequency or amplitude detector of these waves by which the balance condition of 6 relative to 5 may be detected. Unlike the design of FIG. 2 the sensor may contain active circuits with stored energy cells or induction power circuits. Many variations of the passive L-C circuit system of FIGS. 2 and 3 are possible, involving other kinds of variable inductors, variable capacitors, both variable inductors and capacitors, or variable resistors to change the resonant frequency or impedance with pressure. Yet another type of electromagnetic detection of the balance condition would be a simple pair of mechanical electric contacts which close when the $\Delta P = 0$ and opens when $\Delta P \neq 0$, thus completing a passive or active circuit which is detected externally by electromagnetic means. Wide latitude is possible in choice of geometry, size, configuration of components, coil, and ferrite geometrics, and frequency of the design of FIG. 2. The magnetic slug may be replaced by a conductive metal slug to achieve induction change by eddy current detuning. The diaphragm or diaphragms may be convoluted as a speaker or rolling diaphragm or as a usual cylindrical bellows to achieve flexibility. The diaphragm may be metal or metal-coated or made of a variety of strong, impermeable, and flexible materials. Initially, the inner spaces of the sensor may or may not contain fluid. If fluid is used to fill the inner spaces or to act as diaphragm coupling, a simple way of insuring that its amount will remain constant is to make it a water solution of the same ionic concentration as the cerebrospinal fluid and intracellular fluid. In this way, the osmotic pressures are equal inside and outside the sensor and the net diffusion flow across the diaphragms will be zero.

Figure 4:
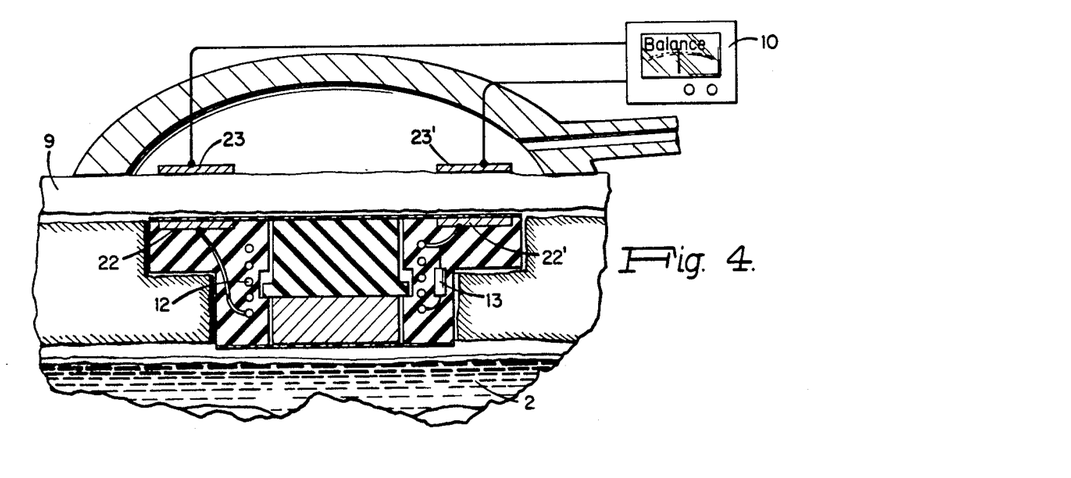
FIG. 4 illustrates capacitive transcutaneous coupling across the skin to an implanted sensor similar to that in FIG. 2.
Figure 5:
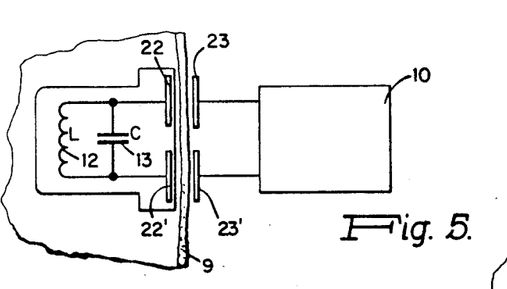
FIGS. 5, 6, 7 and 8 illustrate other sensor and transcutaneous coupling methods.

Referring to FIGS. 4, and 5, an example is shown of a sensor which incorporates an L-C resonant circuit similar to that in FIG. 2 but a different method of electromagnetic coupling across the skin 9 to the external detector system 10. The coupling method is transcutaneous capacitive coupling and is done by area electrodes 22 and 22' near the upper surface of the sensor. These are in proximity to electrodes 23 and 23', respectively, on the skin 4. At the L-C resonant frequency the capacitive reactance of these pairs of adjacent electrodes is small, and thus one can use the resonant frequency of the implanted L-C circuit to determine the frequency of oscillation of an external strongly coupled oscillator housed in 10. This frequency can then be used to indicate the pressure balance condition and the intracranial pressure as discussed above.

It is understood that variants of the transcutaneous coupling scheme of FIGS. 4 and 5 are assumed in this disclosure. For example, whereas in FIGS. 4 and 5 an inductor L and capacitor C are build into the sensor, either one of which or both of which may vary with pressure, it is also possible that only the pressure sensing inductor L, or capacitor C, may be in the implanted sensor, and that the other element of the L-C circuit, C or L respectively, may be in the external system 10 along with the strongly coupled oscillator.

Figure 6:
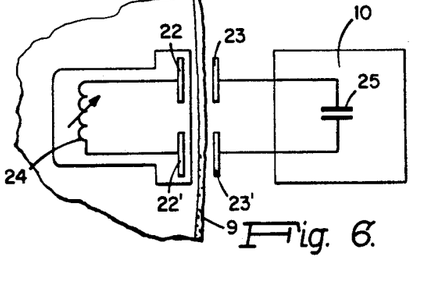

Referring to FIG. 6 the variable pressure sensing inductor 24 is coupled transcutaneously by area electrode pairs 22 and 22' and 23 and 23' to an external capacitor 25 which is integrated into the active external oscillator system that is contained in the external detection system 10. The frequency of oscillations of the external oscillator in 10 is determined by the L-C circuit made up of 24 and 25 and thus determines the balance conditions and intracranial pressure which is read out by 10.

Figure 7:
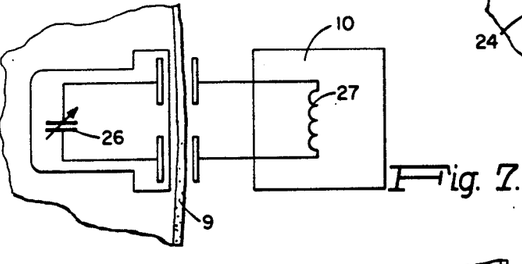

Referring to FIG. 7, the implanted sensor contains the pressure sensitive capacitor 26, and the external active oscillator in 10 contains the complementary inductor 27.

Figure 8:
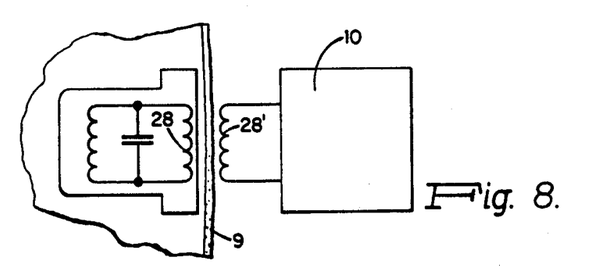

Referring to FIG. 8, the transcutaneous coupling is shown to be inductive rather than capacitive. The implanted L or C may be pressure sensitive, or the implant may contain only L or only C analogously to FIG. 6 and FIG. 7. The implanted coil 28 is coupled to external coil 28', thus achieving the necessary coupling through the skin to the external oscillator in 10. Again, as in designs of FIGS. 5, 6 and 7 the frequency of the external oscillator is determined by the L-C value of the pressure sensitive tank circuit.

Other embodiments of the basic designs disclosed above can be devised for other types of pressure measurements within the body and head. To take as illustrative examples in the case of measuring intracranial pressure, the present invention can be used in conjunction with other functional devices, such as catheters, valves, shunts, flushing devices, reservoirs, filters, anti-siphon devices, and so one, to form a more diverse or multipurpose intracranial pressure monitoring and control system. Some important illustrations are given below.

Figures 9, 10:
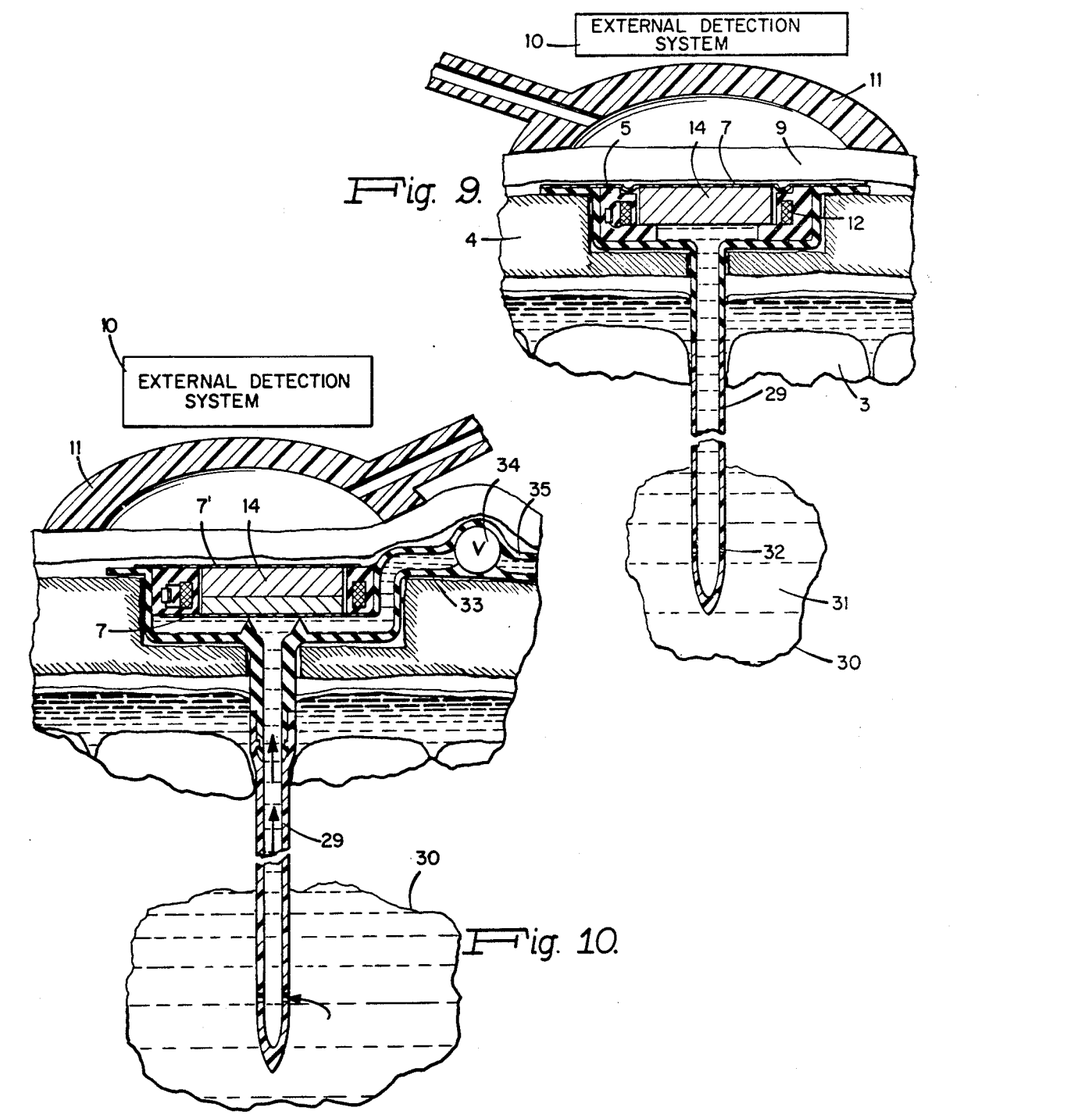
FIG. 9 shows a pressure sensor similar to that of FIG. 2 with specific design variations and an attached catheter.
FIG. 10 shows a combination of the present invention with a catheter and a fluid shunt valve for control of hydrocephalus.

Referring to FIG. 9, the invention is shown connected to a ventricular catheter 29, which penetrates the brain 3 to the depth of the ventrical space 30 and samples the cerebrospinal fluid 31 therein through the holes 32. This device would then measure intraventricular fluid pressure. The catheter is usually made of silicone rubber and is an integral continuation of the encapsulation of the pressure sensor. Some variations in the designs of FIGS. 1 and 2 are also included in FIG. 9. A single diaphragm 7 is used and attached to a ferrite or magnetic cylinder 14 and a thinner geometry of the coil 12 and sensor body 5. In the pressure balanced position the top of the magnetic cylinder 14 is coplanar with the outer table of the skull and its lower rim rests on a shoulder in the body 5. In operation, the hydrostatic pressure of the cerbrospinal fluid acts directly on the bottom side of this single membrane and it must be balanced by an equal external pressure applied through the pressure cuff 11, at which point the resonant L-C circuit's frequency is the balanced frequency $f_o$ as detected by the 10.

Referring to FIG. 10, a sensor of low profile as in FIG. 9 is used with a cathetor 29 which reaches into the ventricular space in the brain and probes the cerebrospinal fluid pressure there. This fluid presses on the lower membrane 7 which is attached to the magnetic slug 14 which in turn is coupled to the upper membrane 7'. Membrane 7' is coplanar with the scalp in the balanced position. The cerbrospinal fluid may be channelled further through tube 33 to a fluid valve 34. Should an excess intraventricular pressure exist, the valve can be opened and the fluid shunted off into the blood stream or elsewhere through the exit tube 35. Shunt valves and ventricular cathetor combinations already exist, however, the combinaion of these with the pressure sensor as in FIG. 10 is a new and unique combination made possible by the present invention concept. Enabling the brain pressure to be read by the sensor is an essential check on the patient status and the proper functioning of the valve. The very low profile of the sensor which is possible with this invention design is of critical importance in such implementations as in FIGS. 9 and 10. It is readily possible to automatically monitor the pressure in an arrangement like that in FIG. 10 and also automatically control the operation of the shunt valve 34 according to whether the pressure is too high or not. It is assumed that such extrapolations and combinations in usage of the present invention are included in the present disclosure.

Figure 11:
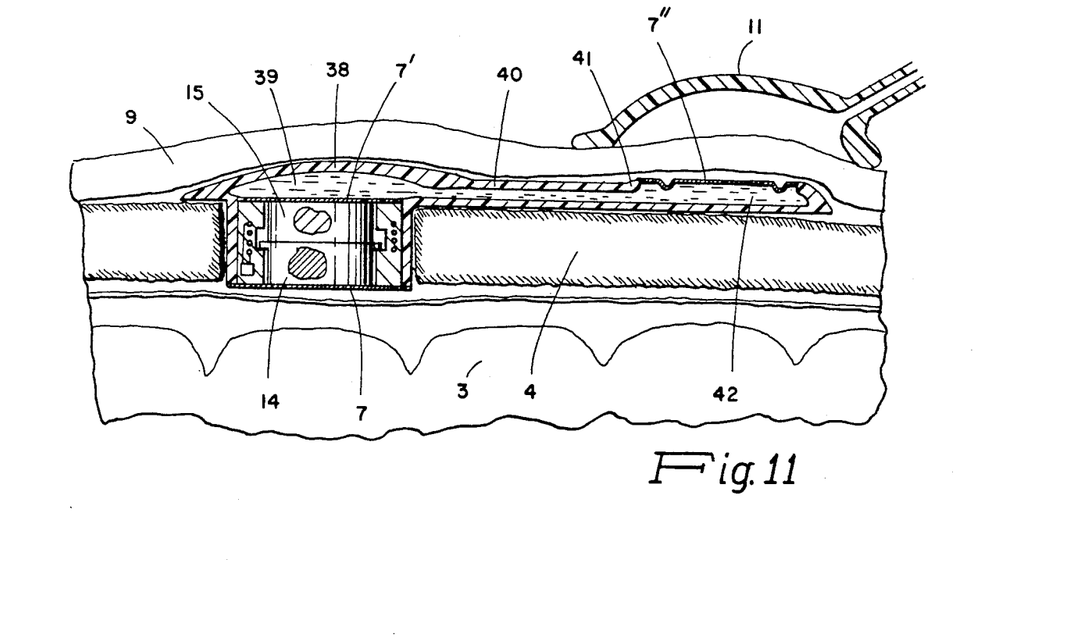
FIG. 11 illustrates another embodiment in which the external balancing pressure is communicated to an upper, flexible diaphragm through a closed fluid system.

Referring to FIG. 11, another embodiment of the invention is illustrated for which the external balancing pressure communicated to the upper flexible diaphragm is supplied by a closed fluid system, rather than directly across the adjacent skin as in FIG. 2. A semi-rigid housing 38 covers diaphragm 7' with a space 39 between them. The housing 38 is connected by a tube 40 to a second housing 41 which lies flat against the skull and which is covered on its upper side by a third flexible diaphragm 7'', thus communicating with the skin above it and thereby with the external pressure on the skin applied by the pressure cuff 11. A fluid fills the volume 39, the tube 40, and the space 42 inside 41. The system is then a triple motion-coupled diaphragm arrangement. The first two diaphragms 7 and 7' plus the magnetic piston 14 and 15 act the same as described above, and the differential pressure on 7 and 7' is sensed by an external detector system. The pressure applied against 7' is now transmitted to it by the fluid filled system comprising 38, 40, 41 and 7''. The applied external pressure on the skin above 7'' will also be transmitted to 7'; and this could serve (a) to zero the magnetic piston 14 plus 15 and thus check the zero-point of the entire system, or (b) to supply a known and calibrated external pressure to 7' so as to balance the internal pressure on 7 and thus measure it by the pressure nulling method.

A configuration similar to that in FIG. 11 is possible where only two flexible diaphragms are used and the differential pressure implant is cathetorized to measure a remote pressure in the ventricles, as was illustrated in FIGS. 9 and 10.

Having described in detail various embodiments of my invention, it will now be apparent to those skilled in the art that numerous modifications can be made therein without departing from the scope of the invention as defined in the following claims. For example, external manipulation of the diaphragm can be achieved by fluidly coupling a pressure source to the diaphragm by means of a fluid filled tube extending through the skin to the diaphragm.

What I claim and desire to secure by Letters Patent of the United States is:

1. A method for measuring an in vivo pressure, said method comprising the steps of:
  (a) implanting in a living body a differential pressure sensor comprising:
    (1) a housing having an opening therein:
    (2) a flexible diaphragm means having a first side and a second side, said flexible diaphragm means extending across said housing opening and being secured with respect to said housing so that when the sensor is implanted in the living body, the first side of said flexible diaphragm means is in
    pressure communication with an internal bodily pressure to be measured and the second side of said flexible diaphragm means is in
    pressure communication with an external variable pressure from a controllable pressure source external to said living body
    and is in mechanical pressure communication with the interior side of a portion of skin whereby the motion of said flexible diaphragm means is responsive to the changes in the difference in said internal bodily pressure and said external variable pressure and the pressure sensor is compensated for atmospheric pressure that is external to the body and in communication with the exterior side of said portion of skin;
    (3) means for defining a mechanical contact reference position with respect to said housing of said flexible diaphragm means, said mechanical contact reference position corresponding to a predetermined pressure relationship between said internal bodily pressure and said external variable pressure;
    (4) means having a preselected, detectable parameter that is detectable by detection means external to said living body, said means having a preselected, detectable parameter being at least in part cooperatively connected to and movable with said flexible diaphragm means so that said preselected, detectable parameter will change with movement of said flexible diaphragm means, said preselected, detectable parameter having a predetermined value at said mechanical contact reference position and said preselected, detectable parameter changing with a displacement from said mechanical contact reference position of said corresponding to a change in said pressures from said predetermined pressure relationship;
  (b) applying a known external variable pressure to said flexible diaphragm means by said controllable pressure source, and varying said known external pressure while detecting said preselected, detectable parameter until said parameter equals said predetermined value at which point said known external variable pressure and said internal bodily pressure have said predetermined pressure relationship.

2. The method of claim 1 further comprising the step of enabling bodily fluid from an internal bodily region to communicate with one side of said flexible diaphragm means such that pressure of said bodily fluid is sensed.

3. A method for measuring an in vivo pressure, said method comprising the steps of:
  (a) implanting in a living body a differential pressure sensor comprising:
    (1) a housing having an opening therein;
    (2) a flexible diaphragm means having a first side and a second side, said flexible diaphragm means extending across said housing opening and being secured with respect to said housing so that when the sensor is implanted in the living body, the first side of said flexible diaphragm means is in
      pressure communication with an internal bodily pressure to be measured and the second side of said flexible diaphragm means is in
      mechanical pressure communication with the interior side of a portion of skin and thereby in pressure communication across the intact skin with a known variable pressure from a controllable pressure source means external to said living body that is adapted to apply mechanical pressure to the exterior side of said portion of skin whereby the motion of said flexible diaphragm means is responsive to the changes in the difference in said internal bodily pressure and said known external variable pressure;
    (3) means for defining a mechanical contact reference position with respect to said housing of said flexible diaphragm means, said mechanical contact reference position corresponding to a predetermined relationship between said pressures in communication with said first and said second sides of said flexible diaphragm means;
    (4) means having a preselected, detectable parameter that is detectable by detection means external to said living body, said means having a preselected, detectable parameter being at least in part cooperatively connected to and movable with said flexible diaphragm means so that said preselected, detectable parameter will change with movement of said flexible diaphragm means, said preselected, detectable parameter having a predetermined value at said mechanical contact reference position, and said preselected; detectable parameter changing with a displacement from said mechanical contact reference position of said flexible diaphragm means corresponding to a change in said pressures from said predetermined pressure relationship;
  (b) varying said known external variable pressure while detecting said preselected, detectable parameter until said parameter equals said predetermined value at which point said known external variable pressure and said internal bodily pressure have said predetermined pressure relationship.

4. The method of claim 3 wherein said flexible diaphragm means comprises a multiplicity of pressure responsive diaphragms that are incompressibly motion coupled together, and further comprising the step of implanting said sensor in the living body so that at least one side of one of said pressure responsive diaphragms is in pressure communication with said internal bodily pressure to be measured, and at least one side of one of said pressure responsive diaphragms is in mechanical contact with said interior side of said portion of skin.

5. The method of claim 3 in which said means for defining a mechanical contact reference position comprises a mechanical stop for at least a portion of said flexible diaphragm means relative to said housing, and further comprising the step of varying said known external variable pressure until said flexible diaphragm means is driven against said mechanical stop.

6. The method of claim 3 wherein said reference position corresponds to the balance of pressures in communication with said first and said second sides of said flexible diaphragm and wherein said known external variable pressure is varied while detecting said preselected, detectable parameter until said parameter equals said predetermined value at which point, said known external variable pressure and said internal bodily pressure are balanced.

7. The method of claim 3 wherein said controllable pressure source means includes a pressure cuff means adapted to be put in contact with said exterior side of said portion of skin, said method further comprising the steps of placing said pressure cuff in contact with the exterior side of said portion of skin and applying said known external pressure to the skin through said pressure cuff.

8. The method of claim 7 wherein at least a portion of said external detection means and said pressure cuff means comprise an integral unit so that when said pressure cuff means is placed in contact with the exterior side of said portion of skin, said portion of the external detection means is positioned in proximity to said portion of skin.

9. The method of claim 3 wherein said controllable pressure source means includes a mechanical force applicator means that can apply a known, variable force to the exterior side of said portion of skin, said variable force being relatable to an equivalent variable pressure on said sensor, and said method further comprising the step of placing said mechanical force applicator means in contact with the exterior side of said portion of skin whereby a variable force can be transmitted through the skin to the sensor.

10. The method of claim 9 wherein at least a portion of said external detection means and said mechanical force applicator means comprise an integral unit so that when said mechanical force applicator means is placed in contact with the exterior side of said portion of skin, said portion of the external detection means is positioned in proximity to said portion of skin.

11. The method of claim 3 wherein said external controllable pressure source means includes an automatic pressure control and readout means which comprises means for automatically varying said external pressure and cooperating automatically with said external detection means, said method further comprising the step initiating the automatic variation of said external pressure whereby when said predetermined value of said detectable parameter at said reference position has been reached, said pressure control means will automatically give a readout of said internal bodily pressure to be measured.

12. The method of claim 3 wherein said means having a preselected detectable parameter comprises electronic circuit means, said preselected, detectable parameter being a characteristic response parameter of said electronic circuit means and detecting said characteristic response parameter by electromagnetic coupling said electronic circuit means to an electronic apparatus means located external to said living body.

13. The method of claim 12 wherein said electronic circuit means comprises a resonant electronic circuit, and said preselected, detectable parameter being a parameter of the resonant frequency response of said resonant circuit and detecting the parameter of the resonant frequency of said resonant circuit.

14. The method of claim 13 wherein said resonant electrical circuit is a parallel resonant circuit and said preselected detectable parameter is the resonant frequency of said parallel resonant circuit and detecting the resonant frequency of said parallel resonant circuit.

15. The method of claim 3 wherein said means having a preselected detectable parameter includes an effective scatterer of ultrasonic waves which moves with said flexible diaphragm means, said external detection means comprises a source of ultrasonic radiation and a detector of ultrasonic radiation whereby differences in frequencies of source and detected radiation can be detected, and said preselected detectable parameter is the shift in frequency of radiation scattered off said scatterer, said value of said frequency shift being zero when said flexible diaphragm is driven against said mechanical stop and said frequency shift being non-zero upon changes in displacement of at least a portion of said flexible diaphragm means with respect to said housing in response to changes in said pressures in communication with said diaphragm means, said method further comprising the steps of irradiating said scatterer with ultrasonic radiation and detecting the differences in frequencies of the irradiated and scattered ultrasonic radiation.

16. The method of claim 3 further comprising the step of precalibrating said predetermined value of said preselected, detectable parameter at said reference position prior to implantation of said sensor in said living body.

17. The method of claim 3 wherein said preselected, detectable parameter is a variable parameter, the variable parameter changing as a known function of said pressures in communication with said flexible diaphragm and further comprising the step of detecting the value of said variable parameter.

18. A method for measuring an in vivo pressure and of calibrating a differential pressure sensor in vivo, said method comprising:
 (a) implanting in a living body the differential pressure sensor comprising:
  (1) a housing having an opening therein;
  (2) a flexible diaphragm means having a first side and a second side, said flexible diaphragm means extending across said housing opening and being secured with respect to said housing so that when the sensor is implanted in the living body, the first side of said flexible diaphragm means is in
   pressure communication with an internal bodily pressure to be measured and the second side of said flexible diaphragm is in
   pressure communication with an external variable pressure from a controllable pressure source external to said living body
   and is in mechanical pressure communication with the interior side of a portion of skin whereby the motion of said flexible diaphragm means is responsive to the changes in the difference in said internal bodily pressure and said external variable pressure and the pressure sensor is compensated for atmospheric pressure that is external to the body and in communication with the exterior side of said portion of skin;
  (3) means for defining a mechanical contact reference position with respect to said housing of said flexible diaphragm means, said mechanical contact reference position corresponding to a predetermined pressure relationship between said internal bodily pressure and said external variable pressure;
  (4) means having a preselected, detectable parameter that is detectable by detection means external to said living body, said means having a preselected, detectable parameter being at least in part cooperatively connected to and movable with said flexible diaphragm means so that said preselected, detectable parameter will change with movement of said flexible diaphragm means, said preselected, detectable parameter changing upon at least a displacement from said mechanical contact reference position of said flexible diaphragm means, said displacement corresponding to a change in said pressures from said predetermined pressure relationship;
 (b) manipulating said sensor by applying a mechanical pressure to the exterior side of said portion of skin to cause said flexible diaphragm means to assume said mechanical contact reference position;
 (c) remotely detecting the value of the preselected, detectable parameter when said flexible diaphragm means is at said mechanical contact reference position without any connection to the sensor that requires a break in the skin;
 (d) applying a known external variable pressure to said flexible diaphragm means by said controllable pressure source and varying said external variable pressure until the value of said preselected, detectable parameter equals the previously detected value at the mechanical contact reference position at which point said external pressure and said internal bodily pressure have said predetermined pressure relationship.

19. A method for measuring an in vivo pressure and of calibrating in vivo a differential pressure sensor, said method comprising:
 (a) implanting in a living body the differential pressure sensor comprising;
  (1) a housing having an opening therein;
  (2) a flexible diaphragm means having a first side and a second side, said flexible diaphragm means extending across said housing opening and being secured with respect to said housing so that when the sensor is implanted in the living body, the first side of said flexible diaphragm means is in
   pressure communication with an internal bodily pressure to be measured and the second side of said flexible diaphragm means is in
   mechanical pressure communication with the interior side of a portion of skin and thereby in pressure communication across the intact skin with a known variable pressure from a controllable pressure source means external to said living body that is adapted to apply a mechanical pressure to the exterior side of said portion of skin whereby the motion of said flexible diaphragm means is responsive to changes in the difference in said internal bodily pressure and said known external variable pressure;

(3) means for defining a mechanical contact reference position with respect to said housing of said flexible diaphragm means said mechanical contact reference position corresponding to a predetermined relationship between said pressures in communication with said first and second sides of said flexible diaphragm means;

(4) means having a preselected, detectable parameter that is detectable by detection means external to said living body, said means having a preselected, detectable parameter being at least in part cooperatively connected to and movable with said flexible diaphragm means so that said preselected, detectable parameter will change with movement of said flexible diaphragm means, said preselected, detectable parameter having a predetermined value at said mechanical contact reference position, and said preselected, detectable parameter changing with a displacement from said mechanical contact reference position of said flexible diaphragm means corresponding to a change in said pressures from said predetermined pressure relationship;

(b) manipulating said sensor by applying a mechanical pressure to the exterior side of said portion of skin to cause said flexible diaphragm means to assume said mechanical contact reference position;

(c) remotely detecting the value of the preselected, detectable parameter when said flexible diaphragm means is at said mechanical contact reference position without any connection to the sensor that requires a break in the skin;

(d) applying a known external variable pressure to said flexible diaphragm means by said controllable pressure source and varying said external variable pressure until the value of said preselected, detectable parameter equals the previously detected value at the mechanical contact reference position at which point said external pressure and said internal bodily pressure has said predetermined pressure relationship.

20. The method of claim 19 wherein said flexible diaphragm means comprises a multiplicity of pressure responsive diaphragms that are incompressibly motion coupled together, and further comprising the step of implanting said sensor in the living body so that at least one side of one of said pressure responsive diaphragms is in pressure communication with said internal bodily pressure to be measured, and at least one side of one of said pressure responsive diaphragms being in mechanical contact with said interior side of said portion of skin.

21. The method of claim 19 in which said means for defining a mechanical contact reference position comprises a mechanical stop for at least a portion of said flexible diaphragm means relative to said housing, and further comprising the step of varying said known external variable pressure until said flexible diaphragm means is driven against said mechanical stop.

22. The method of claim 19 wherein said mechanical contact reference position corresponds to the balance of pressures in communications with said first and second sides of said flexible diaphragm means, and wherein said known external variable pressure is varied while detecting said preselected, detectable parameter until said parameter equals said predetermined value at which point said known external variable pressure and said internal bodily pressure are balanced.

23. The method of claim 19 wherein said controllable pressure source means includes a pressure cuff means adapted to be put in contact with said exterior side of said portion of skin, said method further comprising the steps of placing said pressure cuff in contact with the exterior side of said portion of skin and applying said known external pressure to the skin through said pressure cuff.

24. The method of claim 19 wherein said controllable pressure source means includes a mechanical force applicator means that can apply a known, variable force to the exterior side of said portion of skin, said variable force being relatable to an equivalent variable pressure on said sensor, and said method further comprising the step of placing said mechanical force applicator means in contact with the exterior side of said portion of skin whereby a variable force can be transmitted through the skin to the sensor.

25. The method of claim 23 wherein at least a portion of said external detection means and said pressure cuff means comprise an integral unit so that when said pressure cuff means is placed in contact with the exterior side of said portion of skin, said portion of the external detection means is positioned in proximity to said portion of skin.

26. The method of claim 24 wherein at least a portion of said external detection means and said mechanical force applicator means comprise an integral unit so that when said mechanical force applicator means is placed in contact with the exterior side of said portion of skin, said portion of the external detection means is positioned in proximity to said portion of skin.

27. The method of claim 19 wherein said external controllable source means includes an automatic pressure control and readout means which comprises means for automatically varying said external pressure and cooperating automatically with said external detection means, said method further comprising the step of initiating the automatic variation of said external pressure whereby when said detected value of said detectable parameter at said reference position has been reached said pressure control means will automatically give a readout of said internal bodily pressure to be measured.

28. The method of claim 19 wherein said means having a preselected, detectable parameter comprises electronic circuit means, said preselected, detectable parameter being a characteristic response parameter of said electronic circuit means and detecting said characteristic response parameter by electromagnetic coupling said electronic circuit means to an electronic apparatus means located external to said living body.

29. The method of claim 28 wherein said electronic circuit means comprises a resonant electronic circuit, and said preselected detectable parameter being a parameter of the resonant frequency response of said resonant circuit and detecting the parameter of the resonant frequency of said resonant circuit.

30. The method of claim 29 wherein said resonant electrical circuit is a parallel resonant circuit and wherein said preselected, detectable parameter is the resonant frequency of said parallel resonant circuit and detecting the resonant frequency of said parallel resonant circuit.

31. The method of claim 19 wherein said means having a preselected, detectable parameter is an effective scatterer of ultrasonic waves which moves with such flexible diaphragm means, said external detection means comprises a source of ultrasonic radiation and a detector of ultrasonic radiation, whereby differences in frequencies of source and detected radiation can be detected, and said preselected detectable parameter is the shift in frequency of radiation scattered of off said scatterer, said value of said frequency shift being zero when said flexible diaphragm is driven against said mechanical stop and said frequency shift being non-zero upon changes in displacement of at least a portion of said flexible diaphragm means with respect to said housing in response to changes in said pressures in communication with said diaphragm means, said method further comprising the steps of irradiating said scatterer with ultrasonic radiation and detecting the differences in frequencies of the irradiated and scattered ultrasonic radiation.

32. The method of claim 19 further comprising the step of enabling bodily fluid from an internal bodily region to communicate with one side of said diaphragm means such that pressure of said bodily fluid is sensed.

33. The method of claim 19 further comprising the step of precalibrating said predetermined value of said preselected, detectable parameter at said reference position prior to implantation of said sensor in said living body.

34. The method of claim 19 wherein said preselected, detectable parameter is a variable parameter, the variable parameter changing as a known function of said pressures in communication with said flexible diaphragm and further comprising the step of detecting the value of said variable parameter.

35. A method for remotely detecting in vivo pressure, said method comprising the steps of:
  (a) implanting in a living body a balanced differential pressure sensor comprising:
    (1) a housing having means defining an opening extending therethrough;
    (2) flexible diaphragm means extending across said housing opening and being secured with respect to said housing, said flexible diaphragm means communicating mechanically with pressures in two separate regions external to the sensor that are separated by the flexible diaphragm means with the pressure in one of the regions being an internal bodily pressure when the sensor is implanted in a living body;
    (3) means for defining a reference position of said flexible diaphragm means with respect to said housing for a predetermined pressure relationship between the pressures in said regions; and,
    (4) means having a preselected, detectable parameter that changes with displacement of said flexible diaphragm means from the reference position, upon a change from said predetermined pressure relationship;
  (b) mechanically manipulating the sensor through the intact skin of the body to change the pressure in one of said separate regions thereby causing the sensor to assume the reference position;
  (c) remotely detecting the value of the parameter when the sensor is in the reference position without any connection to the sensor which requires a break in the skin; and,
  (d) applying a known variable pressure to the sensor through the intact skin while remotely detecting said preselected, detectable parameter until the value of said parameter equals the previously detected value at the reference position at which point the known variable pressure and the internal bodily pressure have said predetermined pressure relationship.

36. A method for remotely detecting in vivo pressure, said method comprising the steps of:
  (a) implanting in a living body a balanced differential pressure sensor comprising:
    (1) a housing having means defining an opening extending therethrough;
    (2) flexible diaphragm means extending across said housing opening and being secured with respect to said housing, said flexible diaphragm means communicating mechanically with pressures in two separate regions external to the sensor that are separated by the flexible diaphragm means with the pressure in one of the regions being an internal bodily pressure when the sensor is implanted in a living body;
    (3) means for defining a reference position of said flexible diaphragm means with respect to said housing for a predetermined pressure relationship between the pressures in said regions; and,
    (4) means having a preselected, detectable parameter that changes with displacement of said flexible diaphragm means from the reference position upon a change from said predetermined pressure relationship;
  (b) mechanically manipulating the sensor to cause the sensor to assume the reference position;
  (c) remotely detecting the value of the parameter when the sensor is in the reference position without any connection to the sensor which requires a break in the skin; and,
  (d) applying a known variable pressure to the sensor while remotely detecting the variable parameter until the value of the parameter equals the previously detected value at the reference position at which point the known variable pressure and the internal bodily pressure have said predetermined pressure relationship.

37. A method for measuring an in vivo pressure, said method comprising the steps of:
  (a) implanting in a living body a differential pressure sensor comprising:
    (1) a housing having an opening therein;
    (2) a flexible diaphragm means having a first side and a second side, said flexible diaphragm means extending across said housing opening and being secured with respect to said housing so that when the sensor is implanted in the living body, the first side of said flexible diaphragm means is in pressure communication with an internal bodily pressure to be measured and the second side of said flexible diaphragm means is in mechanical pressure communication with the interior side of a portion of skin and thereby in pressure communication across the intact skin with a known variable pressure from a controllable pressure source means external to said living body that is adapted to apply mechanical pressure to the exterior side of said portion of skin whereby the motion of said flexible diaphragm means is responsive to the changes in the difference in said internal bodily pressure and said known external variable pressure;

(3) means for defining a mechanical contact reference position with respect to said housing of said flexible diaphragm means, said mechanical contact reference position corresponding to a predetermined relationship between said pressures in communication with said first and said second sides of said flexible diaphragm means, and said mechanical contact reference position defining means including electrode contacts that touch at the mechanical contact reference position;

(4) electrical circuit means positioned within said sensor and cooperative with said electrode contacts to produce a detectable characteristic response of said electrical circuit means when said electrode contacts touch;

(b) varying said known external variable pressure while detecting for said detectable characteristic response and terminating the varying of said known external variable pressure upon detection of said detectable characteristic response at which point said known external variable pressure and said internal bodily pressure have said predetermined pressure relationship.

38. A method for measuring an in vivo pressure, said method comprising the steps of:

(a) implanting in a living body a differential pressure sensor comprising:

(1) a housing having an opening therein;

(2) a flexible diaphragm means having a first side and a second side, said flexible diaphragm means extending across said housing opening and being secured with respect to said housing so that when the sensor is implanted in the living body, the first side of said flexible diaphragm means is in pressure communication with an internal bodily pressure to be measured and the second side of said flexible diaphragm means is in mechanical pressure communication with the interior side of a portion of skin and thereby in pressure communication across the intact skin with a known variable pressure from a controllable pressure source means external to said living body that is adapted to apply mechanical pressure to the exterior side of said portion of skin whereby the motion of said flexible diaphragm means is responsive to the changes in the difference in said internal bodily pressure and said known external variable pressure;

(3) mechanical stop means for defining a mechanical contact reference position with respect to said housing of said flexible diaphragm means, said mechanical contact reference position corresponding to a predetermined relationship between said first and said second sides of said flexible diaphragm means;

(4) means having a preselected, detectable parameter that is detectable by detection means external to said living body, said means having a preselected, detectable parameter being at least in part cooperatively connected to and movable with said flexible diaphragm means so that said preselected, detectable parameter will change with movement of said flexible diaphragm means, said preselected, detectable parameter varying with variations in the differences in said pressures on the first and second sides of said flexible diaphragm means and said preselected, detectable parameter ceases to vary when said flexible diaphragm means has been driven against said mechanical stop means by an excess of said known external variable pressure beyond said predetermined pressure relationship in one direction;

(b) monotonically varying said known external variable pressure to drive said flexible diaphragm means against said mechanical stop means to produce a transition from variation to non-variation of said preselected variable parameter so that the value of said known external variable pressure at the point of said transition will be in said predetermined pressure relationship with said internal bodily pressure to be measured.

39. A method for measuring an in vivo pressure, said method comprising the steps of:

(a) implanting in a living body a differential pressure sensor comprising:

(1) a housing having an opening therein;

(2) a flexible diaphragm means having a first side and a second side, said flexible diaphragm means extending across said housing opening and being secured with respect to said housing so that when the sensor is implanted in the living body, the first side of said flexible diaphragm means is in pressure communication with an internal bodily pressure to be measured and the second side of said flexible diaphragm means is in mechanical pressure communication with the interior side of a portion of skin and thereby in pressure communication across the intact skin with a known variable pressure from a controllable pressure source means external to said living body that is adapted to apply mechanical pressure to the exterior side of said portion of skin whereby the motion of said flexible diaphragm means is responsive to the changes in the difference in said internal bodily pressure and said known external variable pressure;

(3) means for defining a mechanical contact reference position with respect to said housing of said flexible diaphragm means, said mechanical contact reference position corresponding to a predetermined relationship between said pressures in communication with said first and said second sides of said flexible diaphragm means;

(4) means having a preselected, detectable parameter that is detectable by detection means external to said living body, said means having a preselected, detectable parameter being at least in part cooperatively connected to and movable with said flexible diaphragm means so that said preselected, detectable parameter will change with movement of said flexible diaphragm means, said preselected, detectable parameter having a predetermined value at said mechanical contact reference position, and said preselected, detectable parameter changing with a displacement from said mechanical contact reference position corresponding to a change in said pressures from said predetermined pressure relationship;

(b) increasing said known external variable pressure with time until the time rate-of-change of said preselected, detectable parameter reaches zero, at which time said known external pressure and said internal bodily pressure have said predetermined pressure relationship.

40. A method for measuring an in vivo pressure and of calibrating in vivo a differential pressure sensor, said method comprising:
  (a) implanting in a living body the differential pressure sensor comprising;
    (1) a housing having an opening therein;
    (2) a flexible diaphragm means having a first side and a second side, said flexible diaphragm means extending across said housing opening and being secured with respect to said housing so that when the sensor is implanted in the living body, the first side of said flexible diaphragm means is in pressure communication with an internal bodily pressure to be measured and the second side of said flexible diaphragm means is in mechanical pressure communication with the interior side of a portion of skin and thereby in pressure communication across the intact skin with a known variable pressure from controllable pressure source means external to said living body that is adapted to apply a mechanical pressure to the exterior side of said portion of skin whereby the motion of said flexible diaphragm means is responsive to changes in the difference in said internal bodily pressure and said known external variable pressure;
    (3) means for defining a mechanical contact reference position with respect to said housing of said flexible diaphragm means, said mechanical contact reference position corresponding to a predetermined relationship between said pressures in communication with said first and second sides of said flexible diaphragm means, and said mechanical contact reference position defining means including electrode contacts that touch at the mechanical contact reference position;
    (4) electrical circuit means positioned within said sensor and cooperative with said electrode contacts to produce a detectable characteristic response of said electrical circuit means when said electrode contacts touch;
  (b) manipulating said sensor by applying a mechanical pressure to the exterior side of said portion of skin to cause said flexible diaphragm means to assume said mechanical contact reference position;
  (c) varying said known external variable pressure while detecting for said detectable characteristic response, said detection being performed remotely from said sensor and without any connection to the sensor that requires a break in the skin;
  (d) terminating the varying of said known external variable pressure upon detection of said detectable characteristic response at which point said known external variable pressure and said internal bodily pressure have said predetermined pressure relationship.

41. A method for measuring an in vivo pressure and of calibrating in vivo a differential pressure sensor, said method comprising:
  (a) implanting in a living body the differential pressure sensor comprising:
    (1) a housing having an opening therein;
    (2) a flexible diaphragm means having a first side and a second side, said flexible diaphragm means extending across said housing opening and being secured with respect to said housing so that when the sensor is implanted in the living body, the first side of said flexible diaphragm means is in pressure communication with an internal bodily pressure to be measured and the second side of said flexible diaphragm means is in mechanical pressure communication with the interior side of a portion of skin and thereby in pressure communication across the intact skin with a known variable pressure from a controllable pressure source means external to said living body that is adapted to apply a mechanical pressure to the exterior side of said portion of skin whereby the motion of said flexible diaphragm means is responsive to changes in the difference in said internal bodily pressure and said known external variable pressure;
    (3) mechanical stop means for defining a mechanical contact reference position with respect to said housing of said flexible diaphragm means said mechanical contact reference position corresponding to a predetermined relationship between said pressures in communication with said first and second sides of said flexible diaphragm means;
    (4) means having a preselected, detectable parameter that is detectable by detection means external to said living body, said means having a preselected, detectable parameter being at least in part cooperatively connected to and movable with said flexible diaphragm means so that said preselected, detectable parameter will change with movement of said flexible diaphragm means, said preselected, detectable parameter varying with variations in the differences in said pressures on the first and second sides of said flexible diaphragm means and said preselected, detectable parameter ceasing to varying when said flexible diaphragm means has been driven against said mechanical stop means by an excess of said known external variable pressure beyond said predetermined pressure rlationship in one direction;
  (b) monotonically varying said known external variable pressure; and,
  (c) applying the monotically varying pressure to the exterior side of said portion of skin to drive said flexible diaphragm means against said mechanical stop means to produce a transition from variation to non-variation of said preselected variable parameter so that the value of said known external variable pressure at the point of said transition will be in said predetermined pressure relationship with said internal bodily pressure to be measured.

42. A method for measuring an in vivo pressure and of calibrating in vivo a differential pressure sensor, said method comprising:
  (a) implanting in a living body the differential pressure sensor comprising;
    (1) a housing having an opening therein;
    (2) a flexible diaphragm means having a first side and a second side, said flexible diaphragm means extending across said housing opening and securred with respect to said housing so that when the sensor is implanted in the living body, the first side of said flexible diaphragm means is in pressure communication with an internal bodily pressure to be measured and the second side of said flexible diaphragm means is in mechanical pressure communication with the interior side of a portion of skin and thereby in pressure communication across the intact skin with a known variable pressure from a controllable pressure source means external to said living body that is adapted to apply mechanical pressure to the exterior side of said portion of skin whereby the motion of said flexible diaphragm means is responsive to changes in the difference in said internal bodily pressure and said known external variable pressure;

(3) mechanical stop means for defining a mechanical contact reference position with respect to said housing of said flexible diaphragm means said mechanical contact reference position corresponding to a predetermined relationship between said pressures in communication with said first and second sides of said flexible diaphragm means;

(4) means having a preselected, detectable parameter this is detectable by detection means external to said living body, said means having a preselected, detectable parameter being at least in part cooperatively connected to and movable with said flexible diaphragm means so that said preselected, detectable parameter will change with movement of said flexible diaphragm means, said preselected, detectable parameter varying with variations in the differences in said pressures on the first and second sides of said flexible diaphragm means and said preselected, detectable parameter ceasing to vary when said flexible diaphragm means has been driven against said mechanical stop means;

(b) increasing said known external variable pressure with time; and (c) applying, as a mechanical pressure, said increasing with time known external pressure to the exterior side of said portion of skin until the time rate-of-change of said preselected, detectable parameter reaches zero, at which time said known external pressure and said internal bodily pressure have said predetermined pressure relationship.

* * * * *